United States Patent [19]

Strader

[11] Patent Number: 4,679,443
[45] Date of Patent: Jul. 14, 1987

[54] BELT TESTING DEVICE

[75] Inventor: Don S. Strader, Uniontown, Ohio

[73] Assignee: The Goodyear Tire & Rubber Company, Akron, Ohio

[21] Appl. No.: 888,678

[22] Filed: Jul. 24, 1986

[51] Int. Cl.$^4$ .............................................. G01N 3/08
[52] U.S. Cl. ....................................... 73/826; 73/830; 73/862.44
[58] Field of Search ................. 73/828, 829, 830, 826, 73/831, 832, 834, 835, 862, 862.08, 862.19, 862.39, 862.38, 862.42, 862.44, 862.45, 862.47, 862.48, 856, 858, 159

[56] References Cited

U.S. PATENT DOCUMENTS

| | | | |
|---|---|---|---|
| 201,802 | 3/1878 | Lee | 73/830 |
| 241,099 | 5/1881 | Walden | 73/862.42 |
| 852,963 | 5/1907 | Knott | 73/862.44 |
| 2,857,758 | 10/1958 | Snyder | 73/834 |
| 3,864,953 | 2/1975 | Fletcher et al. | 73/862.39 |

FOREIGN PATENT DOCUMENTS 2512993  9/1976  Fed. Rep. of Germany ........ 78/829

Primary Examiner—Stewart J. Levy
Assistant Examiner—Robert R. Raevis
Attorney, Agent, or Firm—R. D. Thompson

[57] ABSTRACT

There is disclosed a device having a supporting frame with a slot forming a gap in one leg of the frame. A stationary and a rotatable shaft are positioned in the frame on opposite sides of the gap. A belt sample is attached to the shafts and a ratchet assembly applies progressively greater strain on the belt sample. The level of strain is measured by a load cell placed across the gap in the frame to yield a value for the ultimate tensile strength of the belt being tested. The device is portable and provided with a handle serving as a lever for applying progressively greater strain through the ratchet assembly. The device is used to compare the relative strengths of conveyor belting samples at a field location.

5 Claims, 3 Drawing Figures

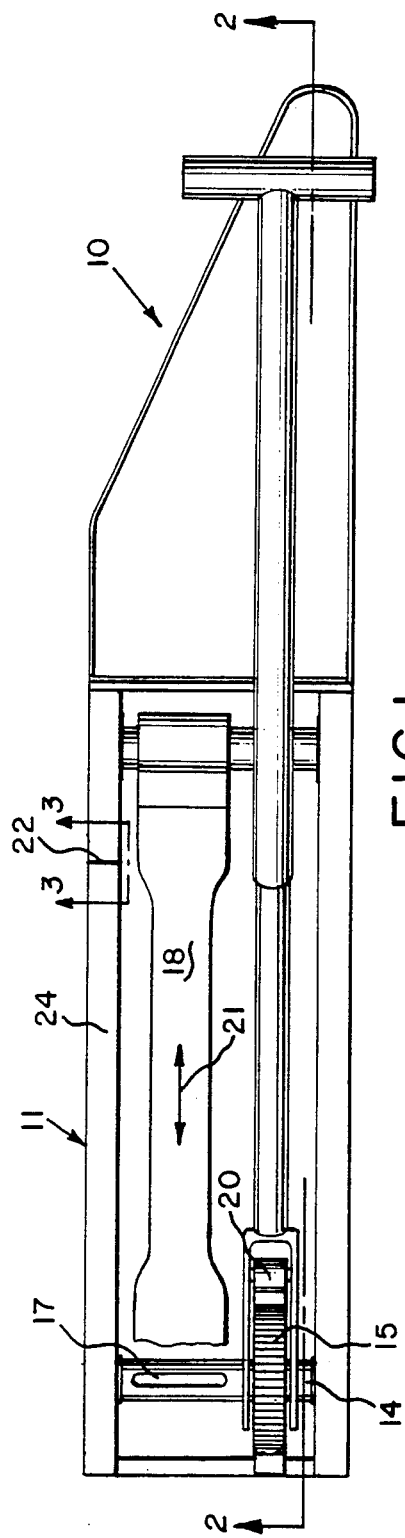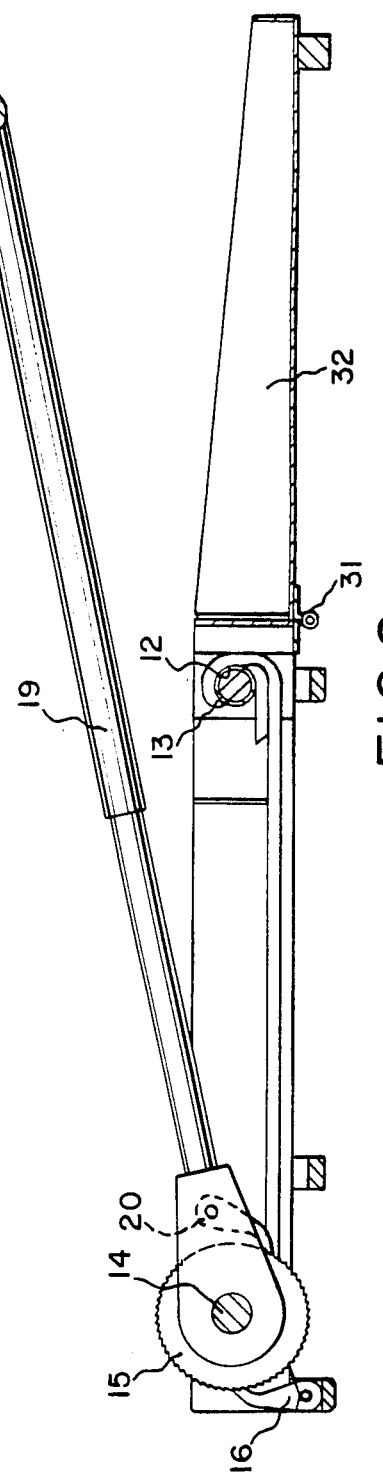

BELT TESTING DEVICE

BACKGROUND OF THE INVENTION

This invention relates to an apparatus for testing the tensile strength of belting, particularly reinforced belting structures such as V-belts and conveyor belts.

The determination of the ultimate tensile strength of belts is an important factor in both system and belt design. In conveyor belting the load capacity of the conveying system is substantially influenced by the ultimate tensile strength of the conveyor belt being utilized. Similarly, in industrial and automotive V-belt applications it is important to determine the amount of idler stress which can be placed on the belt to insure its satisfactory operation. The determination of ultimate tensile strength prior to this invention has been determined by the use of heavy, usually stationary devices which utilize hydraulics and/or electric motors and gears to provide the force required to stress the belt to its tensile failure point. These stationary devices require that samples of the belt be cut and prepared in the field and brought to some central location for subsequent testing. The inconvenience and time delay of such procedures adversely affected the belt users inclination to undertake such testing. Failure to determine the ultimate tensile strength of various belts can result in operating safety problems as well as unnecessary down time associated with belt failures in conveying and power transmission applications.

It is an object of this invention to provide a lightweight, portable apparatus for the testing of ultimate tensile strengths of belt products.

It is a further object to provide a convenient method for testing belts in the field.

It is yet another object of the invention to provide a hand operated simple device which produces repeatable test results in remote field locations.

BRIEF DESCRIPTION OF THE DRAWINGS

FIG. 1 is a top view of the belt testing apparatus showing a partially cut away belt entrained on the apparatus.

FIG. 2 is a cross-sectional view of the apparatus of FIG. 1 taken along line 2—2.

BRIEF DESCRIPTION OF THE INVENTION

Figure 3:
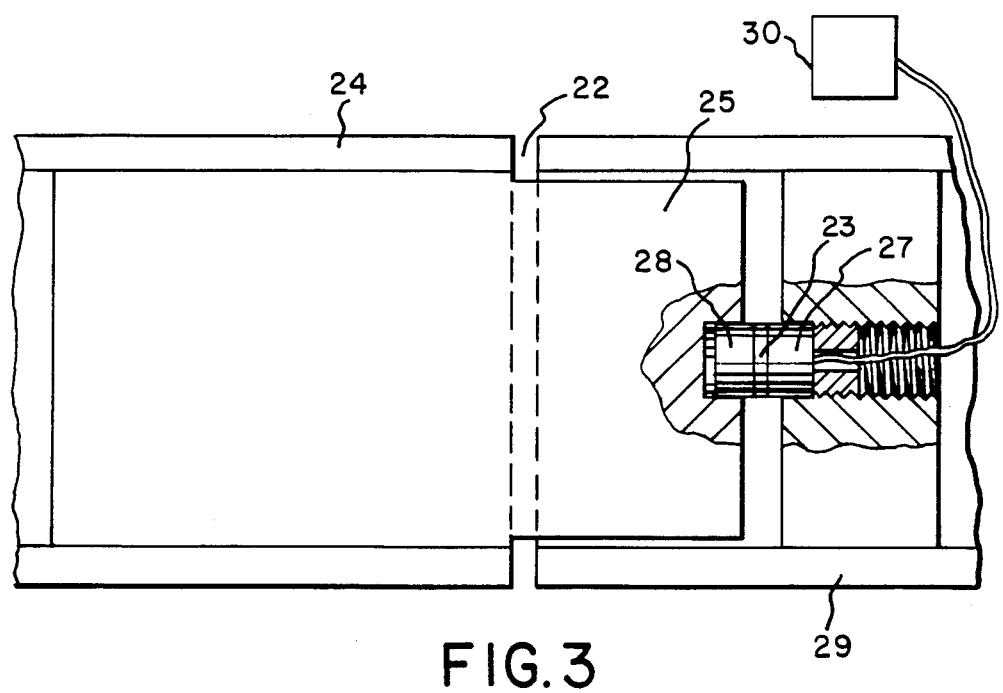
FIG. 3 is an exploded view of a portion of the apparatus taken along line 3—3 of FIG. 1 showing the load cell sensor and the portion of the frame across which the load cell reads.

An embodiment of the invention is a belt testing apparatus comprising: a frame having a pair of spaced apart rails, one of said pair of rails having a gap therein separating said rail into two portions; a stationary shaft rigidly fixed within said frame between said pair of spaced apart rails; a rotatable shaft rotatably positioned within said frame at a predetermined distance from and generally parallel to said stationary shaft, said rotatable shaft being positioned on the opposite side of said gap from said stationary shaft; a means for rotating said rotatable shaft; a strain sensing means positioned across said gap in said frame, said strain sensing means being adapted to sense the amount of strain being exerted on said one of said pair of rails of said frame.

Additional embodiments use a ratchet and pawl assembly as the means for rotation. A compression load cell positioned across the gap in the rail may be preferably used as the strain sensing means.

DETAILED DESCRIPTION OF THE INVENTION

Referring now to FIGS. 1, 2 and 3, the belt testing apparatus 10 is described. A foldable aluminum frame 11 has a stationary shaft 12 with a slot therein 13. A rotatable shaft 14 is journaled into the frame 11 at a distance apart from the stationary shaft 12. The shaft is positioned within bearings to allow free rotation. The rotatable shaft 14 is fitted with ratchet wheel 15 and holding pawl 16. The shaft 14 is provided with a slot 17. A belt sample 18 is inserted through the slot 13 in the stationary shaft and wrapped around the shaft as best shown in FIG. 2. Doubling the belt end over upon itself assures secure fixment of the belt in the stationary shaft. The opposite end of the belt 18 is inserted into slot 17 in the rotatable shaft 14.

Handle 19 is rotatably connected to rotatable shaft 14. Handle 19 also has a carrying pawl 20 which engages the ratchet 15 on the downward stroke of the handle 19 to rotate the shaft 14 and wrap the belt 18 onto the shaft. Holding pawl 16 holds tension on the belt sample by preventing rotation of the shaft 14 while the arm is being moved upward. During the upward motion the carrying pawl 20 rides around on the ratchet teeth without engaging. Downward force exerted on the arm 19 is converted to torque in the shaft 14 by the ratchet arrangement. The tension developed on belt sample 18 is sufficient to break the belt through the narrowed neck portion 21.

One side rail 24 of the frame 11 has a gap 22 which is bridged by a compression type load cell 23. FIG. 3 is an enlarged view of the side rail 24 of the frame 11 which contains the gap 22. FIG. 3 shows the preferred arrangement in which the portion of the side rail 24 which is directly connected to the rotatable shaft 14 has a slider segment 25 which fits slideably within the second portion 29 of the side rail 24 which is connected to the stationary shaft 12 on the opposite side of the gap 22. One side 27 of the load cell 23 is securely fastened to the second portion 29. The opposite side 28 of the load cell is abuttingly engaged against the slider segment 25 which is connected to the portion of the side rail 24 supporting the rotatable shaft 14. The load cell 23 output is connected to a sensing and recording means 30. The sensing and recording means can be any conventional meter suitable to be calibrated for use with an analog or strip recorder to provide data on ultimate tensile strength data during operation.

The foldable embodiment of frame 11 includes a hinge 31 which allows a portion 32 of the frame to be folded for storage and transportation.

During operation of the belt testing apparatus 10, a belt sample 18 having a neckdown portion 21 as shown is threaded into the slots 13 and 17 provided in shafts 12 and 14 respectively. During operation of the testing device the handle 19 is repeatedly forced downward thus rotating and drawing the belt sample 18. As the force is progressively increased during each subsequent circular motion of the ratchet, the tension developed during the ratcheting exerts a reaction force on the side rail 24 of the frame 11 the magnitude of which is registered by the load cell 23 through the gap 22 in the side rail 24. The force is progressively increased until the ultimate tensile stress of the belt is reached and the belt rips in the neck portion 21. The recording means 30 provides the user with a suitable output as to the force level required to rip the belt sample 18.

Any suitable strain sensing means may be utilized to span the gap 22. FIG. 3 illustrates the use of a compression type load cell 23 which is of conventional type utilizing the change in electrical resistance of a coil when placed under varying degrees of compression. The output of such a strain sensing means yields either a direct reading which can be calibrated to give an absolute value for the force required to break the sample or it may yield a relative value which can be used for comparison with other samples to determine which samples are of greater tensile strength. When only a comparative set of readings is required this is described as a proportional sensing reading as compared to an absolute strain value. It should be appreciated by one skilled in the art that the strain sensing means may include other electrical devices or a hydraulic sensor. The hydraulic sensor may utilize a fixed volume reservoir on a piston and the apparatus would sense the hydraulic pressure differential associated with minute changes in the dimension of the gap 22.

A more complex alternative embodiment of this invention would utilize an electrical motor to drive the rotatable shaft 14. The electrical motor of very low speed would be used to replace the ratchet and pawl mechanisms 15, 16 and 20 and obviates the need for the handle 19 to actuate the pawl 20. The motor would provide the motive means for rotating the shaft 14 and eventually breaking the test sample 18.

As noted in FIG. 1, the belt sample being tested is not centered in the frame 11, it is being located somewhat nearer the frame side with the gap 22. This, by virtue of the laws of mechanics, means that when the belt sample is strained, the leg of the frame nearest the sample will carry a larger share of the stress.

In this configuration, the device will provide a stress reading which is proportional to the actual stress in the belt. Different readings from different samples will be directly comparable.

The signal generated can be treated electronically to read the actual stress in the belt sample if this is desired.

The frame could be designed to carry the sample in the center of the span but this is not really necessary to obtain useful data.

While certain specific embodiments and details have been shown for the purpose of illustrating the invention, it will be apparent to those skilled in this art that various changes and modifications may be made therein without departing from the scope of the invention.

What is claimed is:

1. A belt testing apparatus for indirect measurement of tensile strength of a belt sample by direct measurement of the compressive strain on the apparatus, said apparatus comprising:
   a frame having a pair of spaced apart rails, one of said pair of rails having a gap therein separating said one rail into a first portion and a second portion;
   a stationary shaft rigidly fixed within said frame between said pair of spaced apart rails;
   a rotatable shaft rotatably positioned within said frame at a predetermined distance from and generally parallel to said stationary shaft, said rotatable shaft being rigidly fixed at said predetermined distance from said stationary shaft and positioned on the opposite side of said gap from said stationary shaft;
   a means for attaching said belt sample to said stationary shaft and said rotatable shaft;
   a means for rotating said rotatable shaft; and
   a strain sensing means positioned across said gap in said frame, said strain sensing means being adapted to sense the amount of compressive strain being exerted on said one of said pair of rails of said frame, said compressive strain being proportional to said tensile strength of said belt sample.

2. Belt testing apparatus according to claim 1 wherein said means for rotating said rotatable shaft is a ratchet wheel and pawl wherein said ratchet wheel is fixedly attached to said rotatable shaft and said pawl is attached to a handle means adapted to propel said pawl into contact with said ratchet wheel, said handle means being rotatably mounted on said rotatable shaft such that the motion of said handle means propels said ratchet wheel thereby rotating said rotational shaft.

3. A belt testing apparatus according to claim 1 further comprising a slot in said stationary shaft and the slot in said rotatable shaft adapted for receiving a belt sample for testing.

4. A belt testing apparatus of claim 1 wherein said strain sensing means is a compression load cell positioned in said gap and having a sensing end portion abuttingly engaged against said first portion of said one rail and being rigidly fixed to said second portion of said one rail at an end distal said sensing end portion.

5. A belt testing apparatus of claim 4 wherein said compression load cell further comprises a coil producing an electrical resistance reading that varies with the amount of compressive strain on the sensing end portion of said compression load cell.

* * * * *